United States Patent
Grodzki

(10) Patent No.: US 9,684,046 B2
(45) Date of Patent: Jun. 20, 2017

(54) MAGNETIC RESONANCE COIL APPARATUS

(71) Applicant: David Grodzki, Erlangen (DE)

(72) Inventor: David Grodzki, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 680 days.

(21) Appl. No.: 14/098,220

(22) Filed: Dec. 5, 2013

(65) Prior Publication Data

US 2014/0159721 A1    Jun. 12, 2014

(30) Foreign Application Priority Data

Dec. 6, 2012 (DE) .................. 10 2012 222 375

(51) Int. Cl.

| | |
|---|---|
| *G01R 33/56* | (2006.01) |
| *G01R 33/48* | (2006.01) |
| *A61B 5/055* | (2006.01) |
| *A61B 5/11* | (2006.01) |
| *G01R 33/565* | (2006.01) |
| *A61B 5/00* | (2006.01) |
| *G01R 33/34* | (2006.01) |

(52) U.S. Cl.
CPC ............ *G01R 33/48* (2013.01); *A61B 5/0555* (2013.01); *A61B 5/11* (2013.01); *G01R 33/56509* (2013.01); *A61B 5/0077* (2013.01); *G01R 33/34046* (2013.01)

(58) Field of Classification Search
CPC ........ G01R 33/34046; G01R 33/56509; A61B 5/11; A61B 5/0555; A61B 5/0077
See application file for complete search history.

(56) References Cited

U.S. PATENT DOCUMENTS

| | | | |
|---|---|---|---|
| 2007/0280508 A1* | 12/2007 | Ernst | A61B 5/055 382/107 |
| 2008/0029704 A1* | 2/2008 | Hefetz | A61B 6/037 250/363.01 |
| 2009/0209846 A1 | 8/2009 | Bammer | |
| 2010/0198112 A1* | 8/2010 | Maad | A61B 6/0457 600/595 |
| 2012/0320178 A1 | 12/2012 | Siegert et al. | |
| 2014/0051976 A1* | 2/2014 | Rapoport | A61B 5/0077 600/411 |

(Continued)

FOREIGN PATENT DOCUMENTS

DE    102010018899 B4    8/2014

OTHER PUBLICATIONS

A Micro Camera Utilizing a Microlens Array for Multiple Viewpoint Imaging, Aldalali et al, 2011.*

(Continued)

*Primary Examiner* — Clayton E Laballe
*Assistant Examiner* — Ruifeng Pu
(74) *Attorney, Agent, or Firm* — Lempia Summerfield Katz LLC

(57) ABSTRACT

A magnetic resonance coil apparatus includes a receiving region for receiving a subregion of a patient to be examined, a housing shell unit enclosing the receiving region, and an antenna unit for picking up magnetic resonance signals. The magnetic resonance coil apparatus includes a camera unit with at least one light field camera element.

20 Claims, 2 Drawing Sheets

(56) References Cited

U.S. PATENT DOCUMENTS

| | | | | |
|---|---|---|---|---|
| 2014/0070807 A1* | 3/2014 | Biber | ............... | G01R 33/56509 324/309 |
| 2014/0073904 A1* | 3/2014 | Biber | ..................... | A61B 6/527 600/410 |
| 2014/0073908 A1* | 3/2014 | Biber | ............... | G01R 33/56308 600/415 |
| 2014/0125779 A1* | 5/2014 | Ericson | .............. | H04N 13/0402 348/51 |
| 2015/0077113 A1* | 3/2015 | Benner | .................. | A61B 5/721 324/318 |
| 2015/0139515 A1* | 5/2015 | Smith | .................... | A61B 6/032 382/131 |
| 2015/0366527 A1* | 12/2015 | Yu | .......................... | A61B 5/055 382/131 |
| 2015/0381908 A1* | 12/2015 | De Bruijn | ............. | G01J 5/0896 348/253 |
| 2016/0035108 A1* | 2/2016 | Yu | ......................... | G06T 7/2093 382/131 |
| 2016/0038090 A1* | 2/2016 | Heismann | ............ | A61B 5/0059 600/410 |
| 2016/0073962 A1* | 3/2016 | Yu | ......................... | A61B 5/721 600/407 |

OTHER PUBLICATIONS

German Office Action for German Application No. 10 2012 222 375.4, mailed May 8, 2013, with English Translation.
Hilmar Schmundt, "How Insect-Eyed Cameras Could Change Our Lives," Spiegel Online, Jun. 1, 2012, http://www.spiegel.de/international/zeitgeist/mini-insect-eyecameras-and-projectors-could-revolutionize-our-lives-a-836430.html.
Kameragattung der Light-Field-Kameras (LFC) http://en.wikipedia.org/wiki/Light-field_camera_01.06.2012; http://en.wikipedia.org/wiki/Light-field_camera01.06.2012.

* cited by examiner

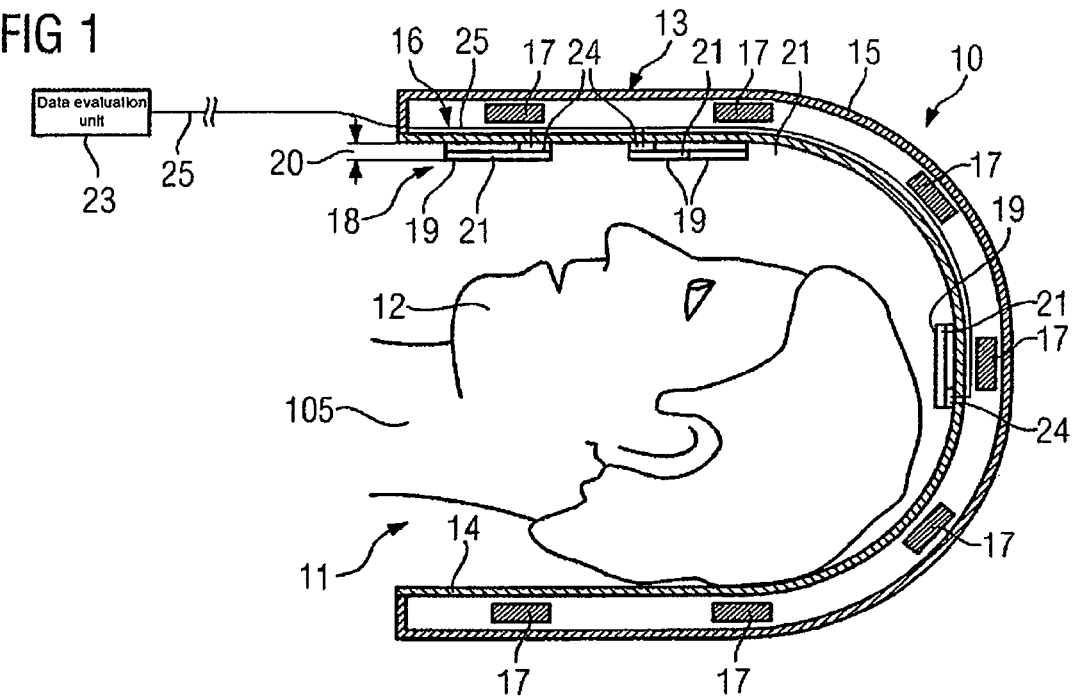
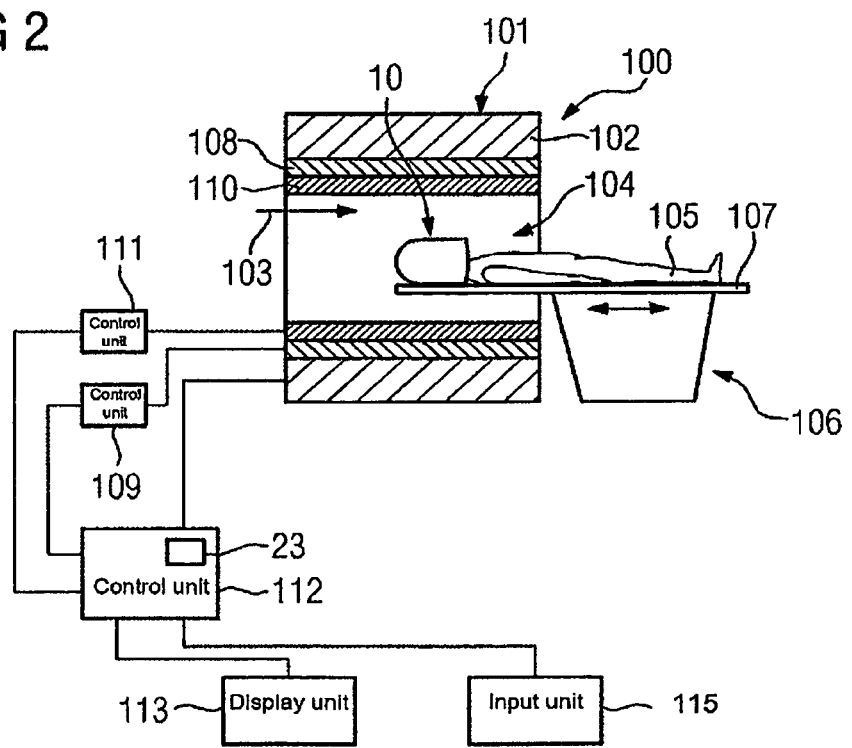

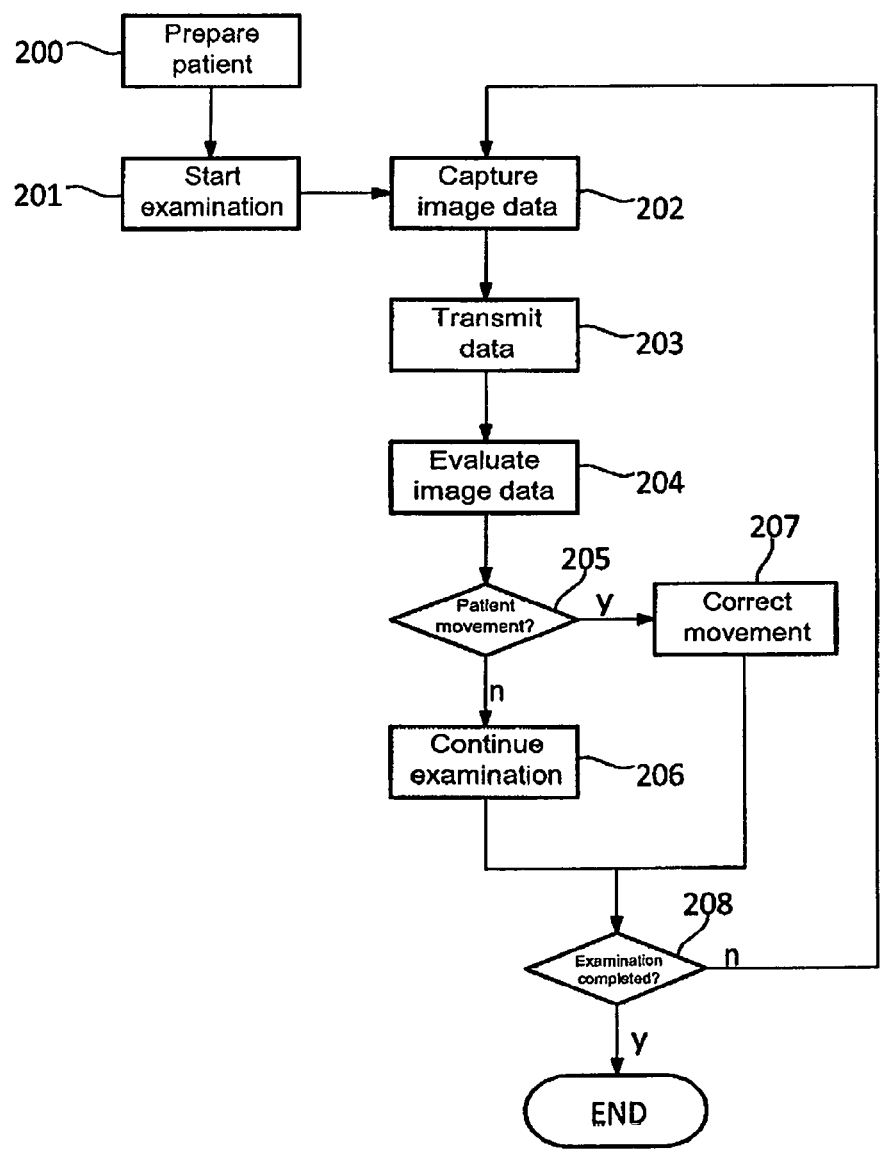

MAGNETIC RESONANCE COIL APPARATUS

This application claims the benefit of DE 10 2012 222 375.4, filed on Dec. 6, 2012, which is hereby incorporated by reference in its entirety.

BACKGROUND

The present embodiments relate to a magnetic resonance coil apparatus.

A magnetic resonance examination may take up to an hour or longer for a patient to be examined. For the duration of a magnetic resonance examination, the patient may lie as still as possible on a patient support apparatus to prevent falsification of the measurement and/or artifacts in the magnetic resonance images.

A distinction is made between two types of patient movement during the magnetic resonance examination: rigid patient movement and non-rigid patient movement. In the case of rigid patient movements, the object to be measured only moves in its entirety. Movement within the object does not take place (e.g., the head of the patient). In the case of non-rigid patient movements, however, the object may also change form and/or move (e.g., the bowel of the patient or a patient's eye movement).

Different approaches have already been adopted for magnetic resonance imaging in order to make the magnetic resonance examination less sensitive with respect to patient movement. A radial acquisition (BLADE), for example, is used for this purpose. Alternatively or additionally, magnetic resonance-based monitoring, with which patient movement is determined by short intermediate scans or navigator scans for locating the patient, may also be used. External marker elements positioned on the patient may also be provided. With the aid of external marker elements, patient movement may be observed from outside by conventional, external camera elements (e.g., using a conventional video camera). The patient movement detected during magnetic resonance measurement is used so that the patient movement results in corrections during postprocessing of the detected magnetic resonance signals. The corrections cancel out patient movements in the measurement data. Information about patient movement (e.g., where the patient movement is significant) also results in the repetition of at least one subregion of magnetic resonance measurement.

The detection of patient movement by external marker elements also uses additional (e.g., externally disposed) optical elements (e.g., a conventional video camera). However, only rigid patient movement may be detected by the external marker elements and the conventional video camera. If local magnetic resonance coils, however, are used for the magnetic resonance examination, movement detection by external marker elements and the conventional, externally disposed video camera may be problematic. For example, an optical field of view of a conventional, externally disposed video camera may be covered by a housing of the local magnetic resonance coil. The arrangement and/or use of conventional, externally disposed video cameras for capturing patient movement data may also impede the magnetic resonance examination, in that the video cameras may restrict the receiving region for the patient because of the size and field of view of the video cameras. Also, because of spatial extension, conventional video cameras may be disposed outside the patient examination region of the magnetic resonance apparatus and/or the local magnetic resonance coil, again impeding the detection of patient movement.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved detection of patient movement during a magnetic resonance examination is provided.

In one embodiment, a magnetic resonance coil apparatus includes a receiving region for receiving a subregion of a patient to be examined, a housing shell unit enclosing the receiving region and an antenna unit for picking up magnetic resonance signals.

The magnetic resonance coil apparatus has a camera unit with at least one light field camera element. A light field camera element refers, for example, to a plenoptic camera element that may capture a 4D light field of a scene or object. In this process, a direction of an incident and/or detected light beam is captured in addition to the position and intensity of the incident and/or detected light beam. The light field camera element and/or the plenoptic camera element has a lattice arrangement made up of a number of microlenses, which is disposed in front of an image sensor. A number of such microlenses may be disposed on a chip, for example.

The at least one light field camera element and/or the at least one plenoptic camera element may be embodied, for example, without a lens system, and/or without an electronic processing system, and/or without mechanical setting technology. A light field camera element and/or a plenoptic camera element may advantageously be used to adjust a focal plane of a recorded image after the image has been captured (e.g., during image data evaluation). Complex focusing on a possible movement region of the patient before recording the image data may also be dispensed with, so that focusing on at least one relevant subregion of the patient may take place after the image data has been captured. This allows the selection of the relevant subregion of the patient to be a function of patient movement during the magnetic resonance examination. Also, a number of movement centers and/or movement regions of the patient may be determined during the evaluation from the image data captured by the camera unit (e.g., image data captured by the at least one light field camera element and/or the at least one plenoptic camera element), and the focus may be on these during the image data evaluation. Movement of the patient within the visual region and/or detection region of the at least one light field camera element may also be detected quickly in this manner. Direct and fast detection of a patient movement may also take place with the aid of marker elements. A position of the marker elements may then be detected using the camera unit (e.g., the at least one light field camera element and/or the plenoptic camera element).

The magnetic resonance coil apparatus may be formed by a high-frequency coil unit integrated in a fixed manner within a magnetic resonance apparatus. Alternatively, the magnetic resonance coil apparatus may also be formed by a magnetic resonance coil apparatus that is only used for one specific application and/or magnetic resonance examination (e.g., of a specific subregion of the patient) for a magnetic resonance examination. The local magnetic resonance coil apparatus may be formed, for example, by a magnetic resonance knee coil apparatus, a magnetic resonance head coil apparatus, a magnetic resonance chest coil apparatus, and/or further local magnetic resonance coil apparatuses.

In one embodiment, the at least one light field camera element is disposed within the receiving region, allowing direct detection and/or monitoring of the patient during the magnetic resonance examination. For example, this allows direct monitoring of a region of relevance for the magnetic resonance examination to be achieved during the magnetic resonance examination. For example, possible movements of the patient may thus be monitored in the subregion of the patient to be examined. The arrangement within the receiving region also allows eye movement of the patient to be detected (e.g., eye tracking; for functional magnetic resonance imaging when using a magnetic resonance head coil imaging apparatus). In one embodiment, a compact magnetic resonance coil apparatus with an integrated camera unit for detecting patient movement may be provided.

It is advantageous that the at least one light field camera element is disposed on the housing shell unit, with a detection region and/or visual region of the light field camera unit facing at least one subregion of the patient. Because of the size, (e.g., the maximum 1 cm thickness) of the at least one light field camera element, a compact and space-saving arrangement of the camera unit within the magnetic resonance coil apparatus may be achieved. This also allows direct monitoring of a subregion of relevance for the magnetic resonance examination to be achieved in a simple manner.

Structurally simple and, for example, cost-saving attachment of the at least one light field camera element within the magnetic resonance coil apparatus may be achieved if the at least one light field camera element is bonded to a side of the housing shell unit facing the receiving region for receiving the subregion of the patient. Alternative ways of attaching the at least one light field camera element to the side of the housing shell unit facing the patient may also be used (e.g., attachment by a welded connection, a form fit connection, a force fit connection, by a further connection method, or a combination thereof) between the at least one light field camera element and the housing shell unit. In one embodiment, the at least one light field camera element may be integrated in the housing shell unit, in that, for example, the housing shell unit has a cutout and/or transparent subregion for the purpose.

In a further embodiment, the camera unit has at least two light field camera elements that are disposed directly adjacent to one another. This allows a large detection area and therefore a large window of vision of the camera unit to be achieved. This is advantageous, as with local magnetic resonance coil apparatuses, a side of the housing shell unit facing the patient is only a few cm away from the patient or is in direct contact with said patient. This also allows a large subregion of the patient to be captured at low cost (e.g., compared with conventional optical elements and/or cameras), allowing effective movement detection during a magnetic resonance examination.

A space-saving arrangement of the at least one light field camera element within the magnetic resonance coil apparatus may be achieved if the at least one light field camera element has a maximum thickness of 5 mm. In one embodiment, the at least one light field camera element has a maximum thickness of 2 mm or approximately 1 mm.

Unwanted impeding of the magnetic resonance examination may be prevented if the at least one light field camera element is configured to be magnetic resonance-compatible. The embodiment of the at least one light field camera element (e.g., without a lens system, without an electronic processing system, without mechanical setting technology, or a combination thereof) allows a simple and low-cost magnetic resonance-compatible embodiment of the camera unit to be achieved.

In one development, the camera unit has a data evaluation unit. Image data captured by the at least one light field camera element is evaluated by the data evaluation unit. This allows fast and direct image data evaluation, which allows patient movement to be detected in a time-saving manner. The data evaluation unit may have the corresponding software and/or computer programs that allow fast image data evaluation with respect to patient movement detection in the image data. The data evaluation unit may also include a processor, storage unit, further units for evaluating the image data, or a combination thereof.

The data evaluation unit may be integrated within the light field camera element, for example, or may also be configured separately from the light field camera element. The data evaluation unit may be disposed within the magnetic resonance coil apparatus. Alternatively, the data evaluation unit may also be integrated within an evaluation unit of the magnetic resonance apparatus and/or may be configured as a single piece therewith.

In one embodiment, the camera unit includes a data transmission unit that transmits the image data captured by the at least one light field camera element, to the data evaluation unit. This allows a secure and, for example, fast data transmission to take place between the at least one light field camera element and the data evaluation unit without thereby influencing a data transmission between the magnetic resonance coil apparatus (e.g., the antenna unit) and a control unit of the magnetic resonance apparatus. The data transmission may take place using fiber optic cables and/or glass fiber cables. The data transmission may also be configured for cableless and/or wireless data transmission.

The magnetic resonance coil apparatus of one or more of the present embodiments (e.g., with the at least one light field camera element and/or the at least one plenoptic camera element) may advantageously be used to adjust a focal plane of a recorded image (e.g., during an image data evaluation). In one embodiment, complex focusing on a possible movement region of the patient before recording the image data may be dispensed with, so that focusing on at least one relevant subregion of the patient may take place after the image data has been captured, allowing the selection of the relevant subregion of the patient to be a function of patient movement during the magnetic resonance examination. Also, a number of movement centers and/or movement regions of the patient may be determined during the evaluation from the image data captured by the camera unit (e.g., image data captured by the at least one light field camera element and/or the at least one plenoptic camera element), and the focus may be on these during the image data evaluation. Movement of the patient within the visual region and/or detection region of the at least one light field camera element may also be detected quickly in this manner.

In one embodiment, a method for detecting patient movement during a magnetic resonance examination with a magnetic resonance coil apparatus is provided. The method includes capturing movement data during the magnetic resonance examination using a camera unit with at least one light field camera element, and transmitting the movement data to a data evaluation unit. The method also includes evaluating the movement data. At least one focal plane is determined in the captured image data during the evaluation act, and at least one patient movement parameter is set.

This allows patient movement to be detected quickly and directly during the magnetic resonance examination (e.g., in a region of relevance for the magnetic resonance examination). It is thus also possible to respond directly to the movement during the magnetic resonance examination (e.g., by changing and/or adjusting a value of a magnetic field gradient and/or by repeating a partial measurement of the magnetic resonance examination). This also minimizes examination times for the patient. In this context, a patient movement parameter refers, for example, to a value and/or parameter that contains information relating to a movement at least of a subregion of the patient. The patient movement parameter may, for example, contain both information about the subregion of the patient that has executed and/or is executing a movement and information about the type of movement, the speed of the movement, the frequency of movement of the subregion of the patient, or a combination thereof, and/or further parameters and/or values relating to a patient movement.

BRIEF DESCRIPTION OF THE DRAWINGS

FIG. 1 shows a schematic representation of one embodiment of a magnetic resonance coil apparatus;
FIG. 2 shows a schematic representation of one embodiment of a magnetic resonance apparatus having the magnetic resonance coil apparatus; and
FIG. 3 shows a schematic representation of one embodiment of a method for detecting patient movement.

DETAILED DESCRIPTION

FIG. 1 shows a schematic representation of one embodiment of a magnetic resonance coil apparatus 10. In one embodiment, the magnetic resonance coil apparatus 10 is formed by a magnetic resonance head coil apparatus 10. Alternatively, the magnetic resonance coil apparatus 10 may also be formed by a magnetic resonance knee coil apparatus, a magnetic resonance chest coil apparatus, a further local magnetic resonance coil apparatus 10, or a combination thereof.

In one embodiment, the magnetic resonance coil apparatus 10 is installed in a fixed manner within a magnetic resonance apparatus 100 (FIG. 2) (e.g., a high-frequency antenna unit 110 that encloses a cylindrical patient examination region 104 of the magnetic resonance apparatus 100).

The magnetic resonance head coil apparatus 10 includes a receiving region 11 for receiving a head 12 of the patient 105 for, for example, head examinations. The magnetic resonance head coil apparatus 10 also includes a housing shell unit 13 that encloses the receiving region 11 in a conical manner. The housing shell unit 13 has a housing shell 14 facing the receiving region 11 and a housing shell 15 (e.g., two housing shells) facing away from the receiving region 11. A space 16 is disposed between the two housing shells 14, 15, in which an antenna unit 17 (e.g., a high-frequency antenna unit) is disposed. The antenna unit 17 is used to pick up magnetic resonance signals that are emitted from the subregion of the patient 105 (e.g., the head 12 of the patient 105) disposed within the receiving region 11 of the magnetic resonance head coil apparatus 10 after stimulation by a magnet unit 101 of the magnetic resonance apparatus 100.

The magnetic resonance head coil apparatus 10 also includes a camera unit 18 that includes a number of light field camera elements 19. The individual light field camera elements 19 are disposed within the receiving region 11 of the magnetic resonance head coil apparatus 10. The individual light field camera elements 19 are disposed on a side of the housing shell unit 13 facing the receiving region 11. The individual light field camera elements 19 are, for example, bonded to the housing shell unit 13 (e.g., to the housing shell 14 facing the receiving region 11).

The individual light field camera elements 19 may, for example, capture a 4D light field of a scene or object. In this process, a direction of an incident and/or detected light beam is captured in addition to the position and intensity of the incident and/or detected light beam. The individual light field camera elements 19 have a lattice 21 made up of a number of microlenses that is disposed in front of an image sensor element. A number of such microlenses may be disposed on a chip, for example. These microlenses are read by the image sensor element (not shown in detail), which may also be disposed on the chip. The individual light field camera elements 19 also have a maximum thickness 20 of, for example, 5 mm, 2 mm, or approximately 1 mm. The small thickness 20 of the light field camera elements 19 provides that the light field camera elements 19 may also be disposed in regions of the receiving region 11 that are in contact with the patient 105 when the patient 105 is disposed within the receiving region 11 or are at a short distance of a few mm from the patient 106 (e.g., in the region of a cover that covers a forehead region of the patient 106, on the housing shell unit 13 within the receiving region 11).

At least two of the several light field camera elements 19 form a closed detection area 22. The at least two light field camera elements 19 are, for example, disposed so that the at least two light field camera elements 19 are directly adjacent to one another, thereby achieving the greatest possible detection area using the individual light field camera elements 19.

The camera unit 18 also includes a data evaluation unit 23 and a data transmission unit 24. The data evaluation unit 23 is used to evaluate the image data captured by the light field camera elements 19 with respect to movement of the patient 105. The captured image data is transmitted from the light field camera elements 19 to the data evaluation unit 23 using the data transmission unit 24. The data transmission unit 24 includes one or more data transmission devices 25 configured, for example, as fiber optic cables and/or glass fiber cables. Alternatively or additionally, one or more further data transmission devices 25 may be provided.

The data evaluation unit 23 is integrated within an evaluation unit and/or control unit 112 of the magnetic resonance apparatus 100 (FIG. 2), so that a detected movement profile of the subregion of the patient 105 disposed within the receiving region 11 of the magnetic resonance head coil apparatus 10 (e.g., the head 12 of the patient 105) may be used directly by the evaluation unit and/or control unit 112 of the magnetic resonance apparatus 100 for the further magnetic resonance examination. Alternatively, the data evaluation unit 23 may be integrated within the local magnetic resonance coil apparatus 10 (e.g., within the space 16 for receiving and/or disposing the high-frequency antenna unit).

The camera unit 18 (e.g., the light field camera elements 19) is also configured to be magnetic resonance-compatible.

FIG. 2 shows a schematic representation of one embodiment of the magnetic resonance apparatus 100. The magnetic resonance apparatus 100 includes a magnet unit 101 having a main magnet 102 for generating a powerful and, for example, constant main magnetic field 103. The magnetic resonance apparatus 100 also includes a cylindrical patient examination region 104 for receiving the patient 105. The patient examination region 104 is enclosed by the magnet unit 101 in a peripheral direction. The patient 105 may be introduced into the patient examination region 104 by a patient support apparatus 106 of the magnetic resonance apparatus 100. The patient support apparatus 106 has a couch 107 that is disposed in a movable manner within the magnetic resonance apparatus 100.

The magnet unit 101 also includes a gradient coil unit 108 for generating magnetic field gradients. The gradient coil unit 108 is used for spatial encoding during imaging. The gradient coil unit 108 is controlled by a gradient control unit 109. The magnet unit 101 also has a fixedly installed high-frequency antenna unit 110 and a high-frequency antenna control unit 111 for stimulating a polarization that becomes established in the main magnetic field 103 generated by the main magnet 102. The high-frequency antenna unit 110 is controlled by the high-frequency antenna control unit 111 and radiates high-frequency magnetic resonance sequences into an examination space that is formed essentially by the patient examination region 104.

For the purpose of controlling the main magnet 102, the gradient control unit 109 and the high-frequency antenna control unit 111, the magnetic resonance apparatus 100 has a control unit 112 formed by a computing unit. The control unit 112 is used for central control of the magnetic resonance apparatus 100, such as performing a predetermined imaging gradient echo sequence, for example. Control information, such as imaging parameters, for example, as well as reconstructed magnetic resonance images, may be displayed on a display unit 113 (e.g., on at least one monitor) of the magnetic resonance apparatus 100 for viewing by an operator. The magnetic resonance apparatus 100 has an input unit 115 by which information and/or parameters may be input by an operator during a measurement procedure.

The magnetic resonance apparatus 100 may include further components that magnetic resonance apparatuses 100 typically include. The general mode of operation of a magnetic resonance apparatus 100 is known to the person skilled in the art, so a detailed description of the general components is not provided.

The magnetic resonance apparatus 100 also includes the local magnetic resonance head coil apparatus 10, as already described in detail in FIG. 1. The magnetic resonance head coil apparatus 10 is used, for example, for head examinations on the patient 105. The head 12 of the patient 105 is supported within the receiving region 11 of the magnetic resonance head coil apparatus 10 for this purpose. The structure and mode of operation of the magnetic resonance head coil apparatus 10 are the same as in the description relating to FIG. 1.

FIG. 3 shows one embodiment of a method for detecting patient movement during the magnetic resonance examination. In a preparation act 200, the patient 105 is first positioned on the patient support apparatus 106 for the magnetic resonance examination. In this process, the head 12 of the patient 105 is also disposed within the local magnetic resonance head coil apparatus 10 (e.g., within the receiving region 11). If required, additional marker elements may also be positioned on the patient 105 (e.g., on the head 12 of the patient 105). The patient 105, together with the movable patient couch 107, is moved into the patient examination region 104.

In a further method act 201, the magnetic resonance examination is started. At the same time, in an image data capturing act 202, data is also acquired by the camera unit 18 (e.g., by the light field camera elements 19). In a transmission act 203, the data from the light field camera elements 19 is transmitted by the data transmission unit 24 to the data evaluation unit 23, where the data is evaluated in an evaluation act 204. In the evaluation act 204, the image data is evaluated with respect to movement of a subregion of the patient 105 (e.g., of the head 12 of the patient 105). A focal plane is also determined, for example, on a selected image plane and/or a selected subregion. In one embodiment, the image plane and/or subregion is selected as a function of a detected movement within at least one subregion of the image data. Also, in the evaluation act 204, at least one patient movement parameter is determined automatically by the data evaluation unit 23. The patient movement parameter includes information about the type of movement and the subregion of the patient 105 executing the movement. The patient movement parameter may also include further information and/or parameters with respect to the detected movement of the patient 105.

The patient movement parameter determined by the data evaluation unit 23 is transmitted by a further data transmission unit (not shown in detail) to the control unit 112 of the magnetic resonance apparatus 100, where the patient movement parameter is taken into account for the control and/or execution of the magnetic resonance examination and/or individual sequence segments. A query 205 then takes place in the control unit 112 as to whether there is patient movement during the magnetic resonance examination, by comparing the patient movement parameter with a threshold value. If there is no movement of the patient 105 during the magnetic resonance examination, or the patient movement parameter is smaller than the threshold value, the magnetic resonance examination is continued without interruption or corrections in method act 206.

If, however, there is patient movement during the magnetic resonance examination, or the patient movement parameter is greater than the threshold value, a correction act 207 is started. The correction act 207 may include, for example, a correction during the evaluation of the magnetic resonance image data. Alternatively or additionally, the correction act 207 may also include termination and/or repetition of individual subsequences. The correction act may be selected automatically by the control unit 112 as a function of the patient movement parameter.

After method act 206 and/or after correction act 207, a query 208 again takes place as to whether the magnetic resonance examination has been completed. If the magnetic resonance examination has been completed, the method for detecting patient movement during the magnetic resonance examination is terminated automatically by the control unit 112. If, however, the magnetic resonance examination has not yet been completed, image data is once again captured by the camera unit 18 (e.g., the light field camera elements 19), so that during the entire magnetic resonance examination on the patient 105, continuous monitoring and control of the patient 105 may always take place with respect to movement of the patient 105 in the subregion of relevance for the magnetic resonance examination.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance local coil apparatus useable within a magnetic resonance device, the magnetic resonance local coil apparatus comprising:
   a receiving region for receiving a subregion of a patient to be examined;
   a housing shell unit enclosing the receiving region;
   an antenna unit operable to pick up magnetic resonance signals from the patient; and
   a camera unit comprising at least one light field camera element directed at the patient;
   wherein the at least one light field camera element is disposed within the receiving region, is disposed on the housing shell unit with a detection region, a visual region, or the detection region and the visual region of the at least one light field camera unit facing at least one subregion of the patient, or is bonded to a side of the housing shell unit facing the receiving region for receiving the subregion of the patient.

2. The magnetic resonance local coil apparatus of claim 1, wherein the at least one light field camera element is disposed within the receiving region.

3. The magnetic resonance local coil apparatus of claim 1, wherein the at least one light field camera element is disposed on the housing shell unit, and
   wherein the detection region, the visual region, or the detection region and the visual region of the at least one light field camera unit face the at least one subregion of the patient.

4. The magnetic resonance local coil apparatus of claim 1, wherein the at least one light field camera element is bonded to the side of the housing shell unit facing the receiving region for receiving the subregion of the patient.

5. The magnetic resonance local coil apparatus of claim 1, wherein the at least one light field camera element comprises at least two light field camera elements that are disposed directly adjacent to one another.

6. The magnetic resonance local coil apparatus of claim 1, wherein the at least one light field camera element has a maximum thickness of 5 mm.

7. The magnetic resonance local coil apparatus of claim 1, wherein the at least one light field camera element has a maximum thickness of 2 mm.

8. The magnetic resonance local coil apparatus of claim 1, wherein the at least one light field camera element is configured to be magnetic resonance-compatible.

9. The magnetic resonance local coil apparatus of claim 1, wherein the camera unit further comprises a data evaluation unit, the data evaluation unit being configured to evaluate image data captured by the at least one light field camera element.

10. The magnetic resonance local coil apparatus of claim 9, wherein the camera unit further comprises a data transmission unit operable to transmit the image data captured by the at least one light field camera element, to the data evaluation unit.

11. A magnetic resonance apparatus comprising:
   a magnet unit;
   a patient examination region for receiving a patient to be examined, the patient examination region being partially enclosed by the magnet unit;
   a magnetic resonance local coil apparatus that is useable within the patient examination region formed by the magnet unit, the magnetic resonance local coil apparatus comprising:
      a receiving region for receiving a subregion of the patient to be examined;
      a housing shell unit enclosing the receiving region;
      an antenna unit operable to pick up magnetic resonance signals from the patient; and
      a camera unit comprising at least one light field camera element arranged relative to the receiving region;
   wherein the at least one light field camera element is disposed within the receiving region, is disposed on the housing shell unit with a detection region, a visual region, or the detection region and the visual region of the at least one light field camera unit facing at least one subregion of the patient, or is bonded to a side of the housing shell unit facing the receiving region for receiving the subregion of the patient.

12. The magnetic resonance apparatus of claim 11, wherein the at least one light field camera element is disposed within the receiving region.

13. The magnetic resonance apparatus of claim 11, wherein the at least one light field camera element is disposed on the housing shell unit, and
   wherein the detection region, the visual region, or the detection region and the visual region of the at least one light field camera unit face at least one subregion of the patient.

14. The magnetic resonance apparatus of claim 11, wherein the at least one light field camera element is bonded to the side of the housing shell unit, facing the receiving region for receiving the subregion of the patient.

15. The magnetic resonance apparatus of claim 11, wherein the at least one light field camera element comprises at least two light field camera elements that are disposed directly adjacent to one another.

16. The magnetic resonance apparatus of claim 11, wherein the at least one light field camera element has a maximum thickness of 5 mm.

17. The magnetic resonance apparatus of claim 11, wherein the at least one light field camera element has a maximum thickness of 2 mm.

18. The magnetic resonance apparatus of claim 11, wherein the at least one light field camera element is configured to be magnetic resonance-compatible.

19. A method for detecting patient movement during a magnetic resonance examination with a magnetic resonance local coil apparatus disposed within a magnetic resonance device, the method comprising:
   capturing movement data during the magnetic resonance examination using a camera unit comprising at least one light field camera element, the at least one light field camera element being disposed within a receiving region enclosed by a housing shell unit of the local coil apparatus, on the housing shell unit with a detection region, a visual region, or the detection region and the visual region of the at least one light field camera unit facing at least one subregion of a patient, or bonded to a side of the housing shell unit facing the receiving region for receiving the subregion of the patient;
   transmitting the movement data to a data evaluation unit; and evaluating the movement data, the evaluating comprising determining at least one focal plane in captured image data and setting at least one patient movement parameter.

20. The method of claim 19, further comprising:
providing the magnetic resonance coil apparatus, the magnetic resonance coil apparatus comprising:
  the receiving region for receiving the subregion of the patient;
  the housing shell unit enclosing the receiving region;
  an antenna unit operable to pick up magnetic resonance signals; and
  the camera unit comprising the at least one light field camera element.

* * * * *